Figure 1:
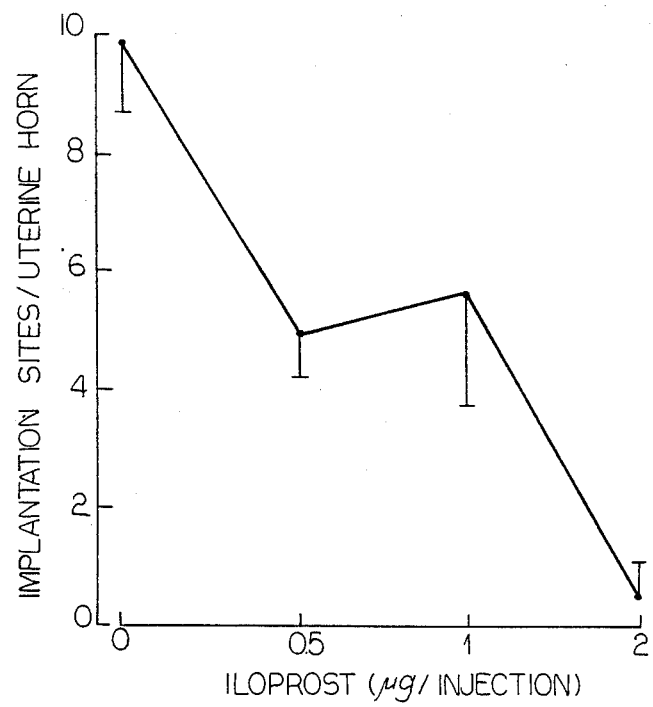

United States Patent [19]

O'Neill

[11] Patent Number: 4,879,285
[45] Date of Patent: Nov. 7, 1989

[54] FERTILITY CONTROL

[75] Inventor: Christopher O'Neill, Greenwich, Australia

[73] Assignee: Royal North Shore Hospital and Area Health Service, St. Leonards, Australia; a part interest

[21] Appl. No.: 86,900

[22] Filed: Aug. 18, 1987

[30] Foreign Application Priority Data

Aug. 22, 1986 [AU] Australia ............................ PH07642

[51] Int. Cl.4 .................. A61K 31/13; A61K 31/557; A61K 31/66
[52] U.S. Cl. ..................................... 514/75; 514/120; 514/841; 514/843
[58] Field of Search ................... 514/841, 843, 75, 120

[56] References Cited

U.S. PATENT DOCUMENTS

| | | | |
|---|---|---|---|
| 3,883,304 | 5/1975 | Hamilton | 436/65 |
| 4,539,332 | 9/1985 | Bifu et al. | 514/471 |
| 4,540,709 | 9/1985 | Chang et al. | 514/470 |
| 4,543,339 | 9/1985 | O'Neill | 436/510 |
| 4,610,687 | 9/1986 | Fogwell | 604/891 |
| 4,619,917 | 10/1986 | Lee et al. | 514/77 |
| 4,665,096 | 5/1987 | Oráa et al. | 514/843 |
| 4,670,426 | 6/1987 | Zor | 514/843 |
| 4,704,462 | 11/1987 | Chang et al. | 548/336 |
| 4,734,280 | 3/1988 | Braguet | 424/195.1 |

OTHER PUBLICATIONS

Baulieu, Etienne-Emile, Contragestion by the Progesterone . . . Control Research in Reproduction vol. 19 No. 1 Jan. 1987, pp. 3-4.

Morris et al, Interception: The Use of Postovulatory Estrogens to Prevent Implantation, Am. J. Obstet. Gyn. Jan. 1, 1973, pp. 101-106.

Primary Examiner—Ronald W. Griffin
Attorney, Agent, or Firm—Ladas & Parry

[57] ABSTRACT

The in-vivo or in-vitro administration of platelet activating factor (PAF) or analogue enhances the viability of fertilized embryos and improves rates of implantation in the uterus. Conversely, reduction of PAF concentration by in-vivo administration of PAF-antagonists such as Iloprost or PAF antibodies, has a contraceptive effect; particularly when used in conjunction with a postcoital contraceptive such as estrogen or a prostaglandin.

19 Claims, 2 Drawing Sheets

FERTILITY CONTROL

The present invention relates to methods and compositions for the control of fertility in mammals by causing artificial changes in the level of platelet activating factor (PAF) which leads to changes in the likelihood of development of a fertilised 1-cell embryo and of implantation in the uterus. specifically, such changes can bring about a contraceptive effect or fertility enhancement.

The term "contraceptive" is used herein in the general sense of an agent capable of the prevention of viable pregnancy. It is known that most species of mammals have a relatively high level of fertilisation, but by comparison relatively few of the fertilised embryos actually implant in the uterus and so result in continuing pregnancies. This implantation failure is probably a major cause of subfertility in humans, particularly women undergoing in-vitro fertilisation and embryo transfer, which is associated with a notoriously high level of implantation failure. Similarly, high productivity losses arise in animal breeding.

Currently there are few successful treatments available for implantation failure. The most widely used method is that of progesterone or gonadotrophin supplementation of the luteal phase. While this may have some beneficial effects in a limited number of circumstances, there does not appear to be a generalised beneficial effect.

Recent work by the present inventor and others (J. Reprod Fert (1985) 73, 559-566 and 567-577; and (1985) 75, 375-380; J. in Vitro Fertil. Embryo Transfer (1985) 2, 87-93; and in Vitro Fertil. Embryo Transfer 442, 429-439) has improved our understanding of the mechanisms of the implantation process. It is found that there is a significant reduction in blood platelet numbers occurring within hours of fertilisation, and this is found to be due to the production of platelet-activating factor by the fertilised embryo.

However, it has not hitherto been established whether this is a chance correlation or whether it represents an essential phenomenon.

The present invention is generally based on our discovery that PAF-mediated pathways are essential to the mechanism of embryo development and implantation.

Platelet activating factor (PAF), 1-Q-alkyl-2-Q-acetyl-sn-glycero-3-phosphocholine, represents a recently defined example of a class of biologically active lipids active in the subnamolar range and possessing a wide spectrum of pathophysiological effects. PAF promotes life-threatening anaphylactic reactions in animals and is suspected of mediating a range of allergic and inflammatory reactions in man. The structure of PAF and analogues showing similar activity has been widely investigated over recent years and is reviewed in a paper by Braquet and Godfroid Platelet Activating Factor, F. Snyder, Plenum Press, publication in August 1987. Naturally occurring PAF has the following structure

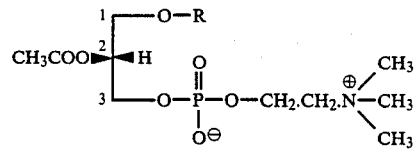

Where R is a $C_{16}$ or $C_{18}$ alkyl group. This paper describes modifications which may be made to the basic structure which effect its platelet activating activity.

The present invention envisages the use of any of such active analogues. The invention also envisages the use of non-active analogues which have no significant platelet activating activity but yet which block PAF receptor sites.

More specifically, one aspect of the present invention provides a method of controlling fertility in a female mammal in-vivo or in-vitro which comprises artificially varying the concentration of PAF or PAF analogue (as herein defined) around the fertilised enbryo so as to control cell division and/or implantation in the uterus.

The term "PAF analogue" is used herein to mean an analogue having a PAF-like effect. Analogues of formula (I) are particularly preferred.

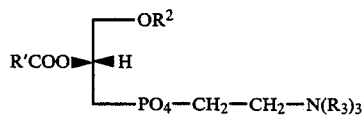

wherein
$R^1$ is $C_{1-6}$alkyl,
$R^2$ is $C_{10-24}$alkyl, and
$R^3$ is $C_{1-3}$alkyl.

In order to increase the chance of implantation (and thus increase fertility) it has been found necessary to increase the in-vivo concentration of PAF, usually by the artificial addition of exogenous PAF or PAF analogue or by reducing the rate of destruction of PAF by acetyl hydrolase; at a time which is post-fertilisation and pre-implantation. In mammals this normally represents a period of 2 to 7 days after fertilisation, and about 6 days in humans. Since PAF itself has a relatively short life time in vivo it is usually necessary to continuously administer PAF throughout that period. However, it has been found that there may be an upper limit to the required PAF level, beyond which higher doses have a deleterious effect on the implantation rate. Thus, the timing and dosage may be important for fertility enhancement.

The invention also provides for enhancing the viability of an in-vitro cultured embryo, which comprises the addition of an effective amount of exogenous PAF or PAF analogue (as herein defined) to culture medium containing the fertilised embryo.

It has been found that the presence of PAF is necessary for development of the 1-cell fertilised embryo to the 2-cell stage.

The invention further provides for the enhancement of implantation in the uterus of an in-vitro cultured embryo, which comprises the administration to the female of an effective amount of exogenous PAF or PAF analogue (as herein defined) prior to the introduction of the embryo into the uterus.

The technology allows for an increase in fertility rates which are of particular benefit in counteracting suboptimal fertility in humans and animals, and is of particular benefit in (i) breeding high cost high predigree animals where implantation rates can be poor.

(ii) transferring embryos from supervulated foster mothers to a surrogate mother, which generally results in a low pregnancy rate.

(iii) intensive breeding programs such as the pig where current implantation failure rate of 30-50% causes enormous economic loss.

A second aspect of the invention provides a method of reducing fertility in a female mammal for the purpose of contraception which comprises the artificial reduction in PAF concentration around the fertilised embryo, or artificial inhibition of PAF-mediated pathways involved in embryo cell division and/or implantation, by the administration to the female of an effectve amount of PAF-antagonist.

Generally speaking, anything which inhibits PAF or the PAF mediated pathways has the potential for contraceptive action. Thus, it has been found that pregnancy may be inhibited by an analogue of the powerful inhibitor of platelet activation $PGI_2$ known as Iloprost. Such treatment completely inhibited the development of pregnancy. Furthermore the inhibition could be overcome by the administration of exogenous PAF. Such inhibitors can be divided into a number of groups by their mechanism of action;

1. Inhibitors of PAF production by the embryo itself e.g. bromophenacylbromide, mepacrine and lipomodulins.

2. Neutralisers of the PAF once it has been produced e.g. antibodies directed against PAF.

3. Substances which block the interaction of the embryo derived PAF with the platelets e.g.
   (i) receptor antagonists, e.g. kadsurenone.
   (ii) inactive PAF analogues which block the PAF binding sites on the platelet cell membrane.

4. Factors which prevent the response of the platelets to PAF e.g. triazolobenzodiazepine drugs such as Alprazolam and Triazolam.

Certain of these pathways, such (2) are less preferred since high concentrations of, for example antibodies, are needed in the system to overcome the localised increase of embryo-derived PAF.

PAF antagonists can be classified as (i) those derived from the PAF structure (ii) naturally occurring PAF-antagonists including chemical derivatives of terpenes, lignans and gliotoxins, and (iii) other agents, with PAF specific actions including some pharmacologically active agents and PAF-acether anti-serum.

(i) PAF related structures:

The most widely used and one of the first PAF antagonists developed is CV-3988 which incorporates an octadecyl carbamate in position 1, a methylether in position 2 and thiazolium ethyl phosphate in position 3. It is orally active in most systems tested and is relatively potent. At very high dose it may antagonise arachidonic acid and ADP activation of platelets.

A heptamethylene thiazolium at $C_3$ gave a potent antagonist termed ONO - 6240. Other minor alterations to this basic structure have been performed by Hoffman La Roche and RO - 19 3704 is the best of these antagonists.

Cyclization of the PAF structure has resulted in another series SRI 63-073 (Sandoz).

Another series is based on the hydrofurone ring and are potent and long acting, SRI 63 441 (Sandoz).

(ii) Naturally Occurring Antagonists

Of the terpenes, Ginkgolides A,B,C,M and T (isolated from *Ginkgo bioloba* L.) are all antagonists with the B (BN 52021) (IHB, Research Labs, France) being most commonly used in PAF antagonist studies.

The best described lignan with PAF antagonist activity is kadsurenone (from Piper Futokadsurae, South China). It is orally active and is reported to have potent antagonist activity in a number of systems. A structural analogue, L-65 2731 (Merck Sharp and Dome) has considerably enhanced potency.

Fermentation of some fungi and micro-organism have produced antagonists which are structurally related to the gliotoxins. The most potent antagonist are FR 900 452 (*S phacofaciens*) and FR - 49175 (*F. testikowski*).

(iii) Other Agents

The triazolobenzodiazepines, particularly Alprazolam and Triazolam potently inhibit PAF activity in vitro. Their action is considerably less in vivo, however, and we have found them not to cause any significant inhibition of implantation in mice. Structural alteration of the triazolobenzodiazepines has resulted in production of numbers of potent antagonists of which WEB 2086 (Boehringer Ingelhelm) is the most widely studied.

An antisera to PAF-acether has been tested and shown to inhibit the biological activity of embryo-derived PAF in vitro and this serum has the ability to partially inhibit implantation.

It has been found to be particularly advantageous to administer the PAF antagonist together with a further post-coital contraceptive agent, such as a prostaglandin, lipoxygenase-blocker, progesterone antagonist, or estrogen.

Prostaglandins which may be useful are Iloprost (an analogue of $PGI_2$) $PGE_2$ and its stable analogues. The latter shares many of the pharmacological properties of $PGI_2$ but is generally less active but more stable in vivo. The prostaglandin $F2\alpha$ is also likely to have a synergistic effect with PAF antagonists in many species, particularly those of agricultural interest $PGF_{2\alpha}$ can terminate early pregnancy via its action on the corpus luteum. This causes loss of progesterone production which in turn leads to the loss of pregnancy.

A group of compounds related to prostaglandins, the lipoxygenase products of arachidonic acid, also are likely to be involved in embryo implantation. This enzyme (lipoxygenase) can be inhibited by compounds such as nardihydroguaiaretic acid (NDGA) and coffeic acid.

Progesterone is the major steroid hormone for the establishment of pregnancy. Its depletion prevents the maintenancy of pregnancy and this can be achieved in a number of ways. Progesterone receptor antagonists include RU 486 (available from Roussel Uclaf under the trademark Mifepristone), ZK 98299 and ZK 98734 (Schering A.G.). These agents competively bind with the progesterone receptor at the target organ (e.g. uterus) and diminish its actions.

Post coital contraception can also be achieved with high dose estrogens. Estrogens can antagonise the actions of progesterone caused by the down regulation of the progesterone receptor by the estrogen. Thus administration of estrogen has the effect of inhibiting progesterone activity and thus pregnancy.

The invention also provides a composition for controlling fertility in a female mammal which comprises an effective amount of PAF or PAF analogue (as herein defined) or an antagonist therefor, together with a pharmaceutically acceptable carrier.

For in-vivo fertility enhancement the composition contains PAF or PAF analogue.

For in-vivo contraception the composition contains a PAF-antagonist, preferably in admixture with a further post-coital contraceptive agent.

The PAF or PAF analogue, or antagonist is preferably administered orally or systemically by intraperitoneal or subcutaneous injection. Alternatively, a sustained release formulation may be used, such as an implant or vaginal pessary.

Embodiments of the present invention will now be described by way of example only.

INHIBITION OF PREGNANCY

EXAMPLE 1

(Platelet activation inhibition)

Figure 2:
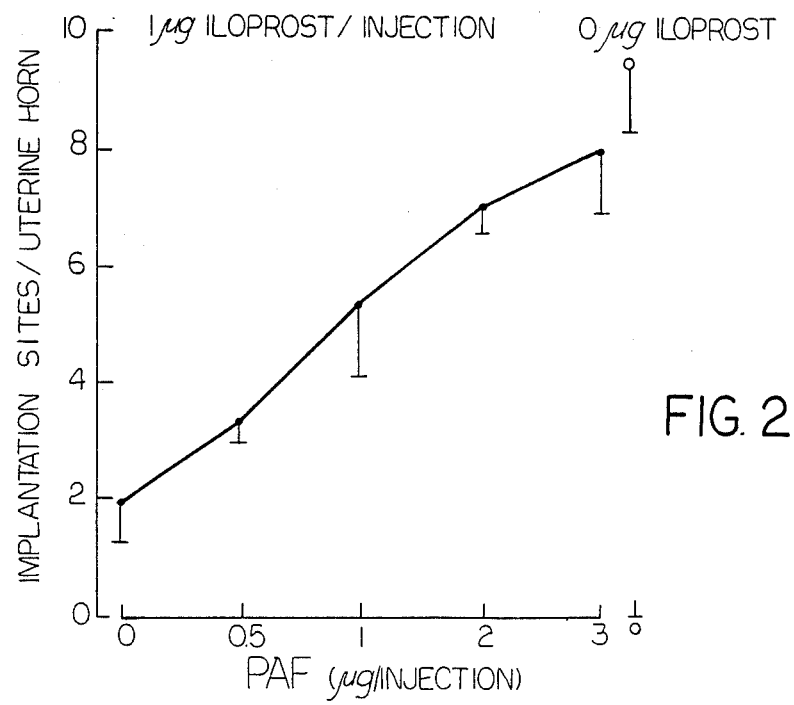

The role of PAF-mediated platelet activation in embryo implantation was investigated by experiments in which platelet activation was inhibited by administration of Iloprost, and wherein activation was restored by injections of PAF. The results are shown in FIGS. 1 and 2.

(a) Iloprost, an analogue of the powerful general inhibitor of platelet activation $PGI_2$, was injected twice daily in amounts of 0.5 to 2.0 micrograms into mice on days 1 to 4 of pregnancy. The mice were sacrificed and the number of implantation sites (i.e. implanted embryos) in the uterus were counted. FIG. 1 shows that pregnancy was completely inhibited by injections of 2.0 micrograms. It is therefore clear that platelet activation has a central role in the implantation mechanism.

(b) Varying amounts of PAF were injected into mice together with 1.0 micrograms of Iloprost. FIG. 2 shows that the platelet deactivation due to the Iloprost can be substantially restored by injection of 3.0 micrograms of PAF. The hollow circle represents a control with no administration of Iloprost or PAF. This clearly establishes the role of the PAF-mediated pathway of platelet activation in the implantation mechanism.

EXAMPLE 2

(Iloprost; and SRI 63441)

The effect of Iloprost and SRI 63441 antagonists on the rate of implantation of embryos was assessed.

Initially, the ability of the antagonists to neutralize PAF-acether induced thrombocytopenia was confirmed in an in-vivo bioassay (O'Neill, J. Reprod. Fertil 73, 567).

Ovulation was synchronized in eight week old Quackenbush strain virgin females with 3iu pregnant mare's serum ganodatrophin by intraperitoneal (i.p.) injection (PMSG, Folligon; Intervet, Boxmeer, The Netherlands) followed, after 48 hours by 3 i.u. human chorionic gonadatrophin (hCG, Chorulin, Intervet). The mice were paired with males of proven fertility, and the presence of a vaginal plug, the next morning, indicated day 1 of pregnancy. Iloprost was administered at concentrations of 0. 0.5, 1.0 and 2.0 ug/30 g body weight in 200 ul phosphate buffered saline (PBS), 1.p at 1600 hours on day 1, 0900 and 1600 hours on days 2 and 3, and 0900 hours on day 4. SRI 63-441 was administered at concentrations of 0, 4.0, 10, 20, and 40 ug/30 g body weight at 1600 hours on day 1 and 0900 hours on days 2-4. Necropsies were performed on day 8 of pregnancy and the number of implantation sites and corpora lutea was determined. Any evidence of embryonic resorption was noted.

To ensure that the effects of the inhibitors were PAF specific, some inhibitor treated animals were simultaneously treated with PAF-acether administered (i.p.) at doses of 0, 0.5 and 1.0 ug/30 g body weight for Iloprost treated animals and at doses of 1.0 and 2.0 ug/30 g body weight for SRI 63 441 treated animals. PAF-acether injections were given at 1600 h on day 1 of pregnancy, 0900 h and 1600 h on days 2 and 3, and at 0900 h on day 4.

Figure 3A:
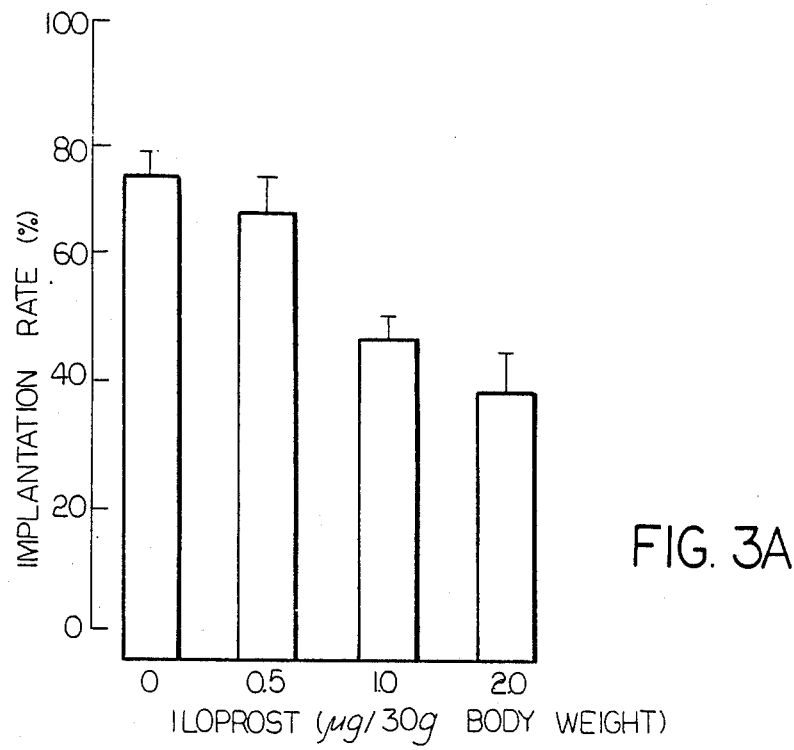
Figure 3B:
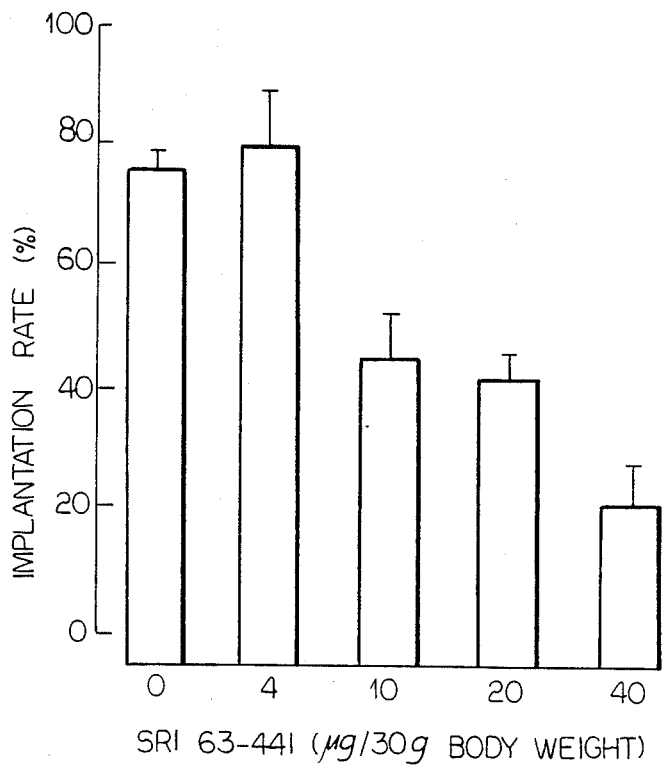

The results are shown on FIGS. 3A and 3B. Doses of 0.5 to 1.0 ug Iloprost, administered over the preimplantation period significantly reduced implantation rates compared with control levels. Similar results were obtained when SRI 63 441 was administered at doses of 10, 20' and 40 ug. The implantation rate is the number of implantation sites/number of corpora lutea. Simultaneous administration of 0.5 ug PAF-acether, with 2.0 ug Iloprost and 1.0 ug PAF-acether with 20.0 ug SRI 63-441 was sufficient to restore implantation rates to levels not significantly different from the controls.

The development of the preimplantation embryos of at least two cells was largely unaffected by the antagonists.

By an analogous method the effect of other PAF antagonists on the rate of implantation was assessed by introperitoneal (i.p.), intravenous (i.v.) and subcutaneous (s.c.) injection and by oral dosage. The results are given in Table 1.

TABLE 1

| Treatment | % Implantations/Ovulation (mean ± S.E.M.) Dose/Mouse/Day | | | | |
|---|---|---|---|---|---|
| SRI 63 675 (i.p.) | 0 77 + 8 | 20 ug 65 ± 6 | | 40 ug 40 ± 9 | |
| SRI 64 557 (i.p.) | 0 60 ± 5 | 20 ug 45 ± 8 | | 40 ug 36 ± 4 | |
| SRI 64 412 (oral) | 0 72 ± 8 | 50 ug 69 ± 5 | 100 ug 65 ± 4 | 400 ug 47 ± 6 | 800 ug 40 ± 6 |
| L652731 (i.p.) | 0 75 ± 8 | 60 ug 57 ± 10 | | 120 ug 51 ± 8 | |
| kadsurenone | 0 70 ± 3 | 60 69 ± 5 | | 120 51 ± 3 | |
| BN 52021 (i.p.) | 0 61 ± 8 | 250 ug 47 ± 5 | | 500 ug 41 ± 6 | |
| Alprazolam | 0 65 ± 3 | 10 ug 60 ± 6 | 50 ug 59 ± 5 | 100 ug 61 ± 6 | |
| Anti-PAF antiserum (i.p.) | 0 65 ± 3 | Antiserum dilute 46% ± 8 | 1/50 | Normal serum 67 ± 4 | non-immune |
| SRI 63 441 (s.c.) | 0 73 ± 4 | 25 ug 59 ± 5 | | 50 ug 33 ± 7 | |
| SRI 63 675 (i.v.) | 0 64 ± 3 | | 75 ug 30 5 ± 8 | | |
| SRI 64 557 (i.v.) | 0 63 ± 5 | | 75 ug 34.8 ± 7 | | |

EXAMPLE 3

(Mixtures of antagonists)

Using the procedure of Example 2 a synergistic effect was demonstrated between the PAF-specific antagonist SRI 63441 and Iloprost.

According to FIGS. 3A and 3B a doubling of the dose of SRI 63441 gives a 12% decrease in implantation rate; and doubling the dose of Iloprost gives a 15% decrease. If the results were additive the effect of the two antagonists together would be expected to be a 27% decrease. However, the experimental results show a 38% decrease as follows, demonstrating a synergistic interaction.

| | % Implantation | | |
|---|---|---|---|
| Control | Iloprost | SRI 63441 | Mixture |
| 71 ± 3 | 60 ± 4 | 62 ± 5 | 44 ± 3 |

Synergism is believed to arise because the antagonists affect different stages in the PAF-mediated pathways. Accordingly synergy is expected with other antagonist combinations.

EXAMPLE 4

(Development of 1-cell embryo) PAF antagonists are also efficient at inhibiting the development of the very early embryo, that is, the further development of the 1-cell embryo. This is demonstrated by two types of experiments. (1) injections of PAF antagonist in the peri-ovulatory phase Mice were synchronized to ovulate by giving 3 iu pregnant mare serum gonadotrophins (PMSG) and 48th later 3 iu human chorionic gonadotrophin (hCG) and then placed with fertile males. If the day of hCG is called Day 0 then i.p. injections of the PAF antagonist SRI 63 441 were given on days −2, −1, 0 and 1. Late on day 1 embryos were collected from the reproductive tract and the ability to develop further was assessed. Doses of 40 ug SRI 63 441/day caused a 70% decrease in the developmental potential compared with control adminals which had saline injections. (2) Animals were superovulated with 10 iu PMSG and HCG and 1-cell embryos were cultured in vitro with various doses of antagonists SRI 63441, SRI 64557 and SRI 63675. The treatments inhibited further development of 1-cell embryos to the 2-cell stage.

Therefore PAF is essential at the two major developmental phases of early pregnancy, (i) cleavage of the one cell embryo and (ii) implantation of the blastocyst, thus providing two sites for contraceptive action at the embryonic level as well as effects via platelets and the maternal reproductive tract.

FERTILITY ENHANCEMENT

EXAMPLE 5

(in vivo)

Exogenous PAF administered during the post-fertilisation/preimplantation phase of pregnancy caused enhanced platelet activation.

PAF was prepared as described in Example 1 and given as intraperitoneal injections twice daily on the first 3 days and on the morning of the 4th day of pregnancy in mice. Mice were autopsied on days 8-9 of pregnancy and the number and condition of the implantation sites examined.

Relatively low doses of the synthetic PAF resulted in a significant increase in both the number of animals that were pregnant and also the number of embryos implanted per pregnant animal. This effect was strictly dose dependent with slightly higher doses having an deleterious effect on the implantation rate. The dosage and route of administration needs to be precisely controlled to determine the beneficial dose for each mammal species used. Such results provide further evidence for (1). The biological similarity of the embryo derived PAF and the synthetic PAF, and (2) the benefical effect of platelet activation (at modest levels) on the establishment of pregnancy. The results are given below.

These results also show that, with carefully controlled administration of PAF, the substance can be used to promote implantation and the establishment of pregnancy.

The effect of PAF-acether administration throughout the preimplantation stage of pregnancy on the pregnancy and implantation rate is shown. Twelve animals were given 0.3 ug injections (i.p.) of PAF or vehicle once daily for the first 4 days of pregnancy.

| | PAF | Control |
|---|---|---|
| % pregnant on Day 8 | 98 | 73 |
| No. of implantations per animal | 12.6 | 7.8 |
| No. of implantations per pregnancy | 13.7 | 10.7 |

EXAMPLE 6

(in-vitro)

Mice were superovulated with gonadotrophins and mated with fertile males 2-cell embryos were collected and cultured for 72 h in human tubal fluid medium (HTFM) containing 3 mg bovine serum albumin/ml and supplemented with 0, 0.1 or 1ug PAF (Sigma Chemicals) per ml of medium. The embryos were cultured in approximately 20 ul drops. After 72h the majority of embryos had developed to the blastocyst stage and were then transferred to uterus of recipients.

Recipients were pseudopregnant females mated with vasectomised males and transfers were performed on Day 3 of pseudopregnancy. Pseudopregnant females were anaesthetised with Avertin or Nembutal (doses as above). A medial dorsal incision was made through the skin, then a smaller incision made throught the body wall over the ovary. The uterine horn was exposed by pulling on the ovarian fat pad. A needle and thread was passed through the mesenteries to aid in holding the uterus. The embryos were then transferred to the uterus through a micropipette inserted towards the vagina through a hold punctured in the cranial end of the uterus with a 26 g needle. The skin incision was stapled with Michel clips (7.5 mm) and a drop of Phisohex applied. 10 blastocysts were transferred to each uterine horn of each mouse. One horn received embryos grown in OugPAF (control) and the other uterine horn had PAF treated (0.1) or 1 ug/ml) embryos.

On day 8 the animals were sacrificed, the uterus exposed and the number of implanted embryos recorded.

| Implantation Rate (% embryos transferred) | | |
|---|---|---|
| | Control Horn | PAF horn |
| 0.1 ug PAF | 34.3 ± 6.1 | 58.6 ± 7.6 |
| 1.0 ug PAF | 29.7 ± 5.4 | 46.1 ± 6.8 |

Thus, the implantation rate of embryos cultured in the presence of PAF was increased over the control.

EXAMPLE 7
(uterus preparation)

The effect of PAF on the progesterone secreting tissue, the corpus luteum, is demonstrated. In many species (particularly agriculturally important species) following superovulation, the production of progesterone by this tissue stops prematurely. This results in the failure of implantation or the early loss of the conceptus. Maintenance of the corpus luteum (CL) therefore enhances fertility. The earliest signal from the embryo which promotes maintenance of the CL is not known but our recent studies suggest that it is in fact PAF. Injection of PAF (200 ug/day) into the uterus of border/leicester cross-breed sheep ewes from days 10–18 of pregnancy resulted in a prolongation of the life span of the corpus luteum of at least 5 days and significantly elevated the peripheral progesterone concentration (10%). These effects could also be demonstrated in the mouse with i.p. injections of PAF which also resulted in a significant elevation in the peripheral concentration in the progesterone concentration. These results are confirmed by our recent observations that the cells of the corpus luteum (granulosa cells) make more progesterone in vitro when PAF is present in the culture medium.

In the mouse this was also manifested in an increase in the uterine weight and therefore presumably in the uterine preparation for pregnancy.

| Effect of PAF on mouse uterine weight (Day 4) | | |
|---|---|---|
| Pseudopregnancy | | Pregnancy |
| PBS | PAF | PBS |
| Uterine wt 139 ± 2.6 | 159.9 ± 2.6 | 159.6 ± 5.6 |

I claim:

1. A method of controlling fertility in a female mammal in-vivo or in-vitro which comprises artificially varying the concentration of platelet activating factor (PAF) or PAF analogue around the fertilized embryo so as to control cell division and/or implantation in the uterus.

2. A method according to claim 1 for the invivo enhancement of mammalian fertility which comprises the administration of an effective amount of exogenous PAF or PAF analogue to the mammal at a time which is post-fertilization and prior to implantation of the fertilized embryo in the uterus.

3. A method according to claim 1 for the enhancement of viability of an in-vitro cultured embryo, which comprises the addition of an effective amount of exogenous PAF or PAF analogue to culture medium containing the fertilized embryo.

4. A method according to claim 1 for the enhancement of implantation in the uterus of an in-vitro cultured embryo, which comprises the administration to the female of an effective amount of exogenous PAF or PAF analogue prior to the introduction of the embryo into the uterus.

5. A method according to claim 1 of reducing fertility in a female mammal for the purpose of contraception which comprises the artificial reduction in PAF concentration around the fertilised embryo, or artificial inhibition of PAF-mediated pathways involved in embryo cell division and/or implantation, by the administration to the female of an effective amount of PAF-antagonist.

6. A method according to claim 5 wherein the PAF-antagonist is selected from the group consisting of (a) inhibitors of PAF production,
(b) PAF antibodies,
(c) substances which block PAF-mediated pathways involved in embryo cell division and/or implantation, and
(d) inhibitors of PAF-mediated platelet activation.

7. A method according to claim 6 wherein the PAF-antagonist is selected from kadsurenone, alprazolam, iloprost, SR1 63 441, SRI 63 675, SRI 64 412, SRI 64 557, L 652 731, and BN 52021.

8. A method according to claim 5 wherein the PAF-antagonist is administered together with an effective amount of a further post-coital contraceptive agent.

9. A method according to claim 8 wherein the further post-coital contraceptive agent is selected from the group consisting of prostaglandins, lipoxygenase-blockers, progesterone antagonists and estrogens.

10. A method according to claim 9 wherein the progesterone antagonist is selected from the group consisting of RU 486, ZK 98299, and ZK 98734.

11. A method according to claim 1 wherein the alkyl groups of PAF may be the same as or different from naturally occurring PAF and at least one alkyl group is different.

12. A method according to claim 1 wherein the PAF analogue has the following formula:

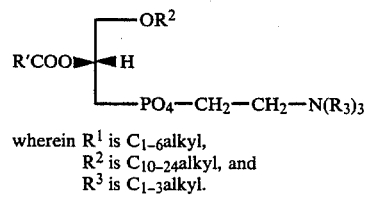

wherein $R^1$ is $C_{1-6}$alkyl,
$R^2$ is $C_{10-24}$alkyl, and
$R^3$ is $C_{1-3}$alkyl.

13. A method according to claim 1 wherein the platelet activating factor is naturally occurring PAF, 1-O-hexadecyl/octadecyl-2-O-acetyl-sn-glycero-3-phosphorylcholine.

14. A contraceptive composition for reducing fertility in a female mammal which comprises an effective amount of an antagonist for 1-O-alkyl-2-O-acetyl-sn-glycero-3-phosphocholine (platelet activating factor-PAF), and an effective amount of a further post-coital contraceptive agent, together with a pharmacetically acceptable carrier.

15. A composition according to claim 14 for use as a contraceptive in a female mammal which comprises effective amount of a PAF-antagonist.

16. A composition according to claim 15 wherein the PAF-antagonist is selected from the group consisting of (a) inhibitors of PAF production,
(b) PAF antibodies,
(c) substances which block PAF-mediated pathways involved in embryo cell division and/or implantation, and
(d) inhibitors of PAF-mediated platelet activation.

17. A composition according to claim 16 wherein the PAF-antagonist is selected from kadsurenone, alprazolam, iloprost, SRI 63 441, SRI 63 675, SRI 64 412, SRI 64 557, L 65237 and BN 52021.

18. A composition according to claim 14 wherein the further post-coital contraceptive agent is selected from the group consisting of prostaglandins, lipoxygenase-blockers, progesterone antagonists, and estrogens.

19. A composition according to claim 18 wherein the progesterone antagonist is selected from the group consisting of RU 486, ZK 98299, and ZK 98734.

* * * * *